United States Patent

Ishiwatari

[11] Patent Number: 6,024,973
[45] Date of Patent: Feb. 15, 2000

[54] FABRIC PROTECTANT

[75] Inventor: Takao Ishiwatari, Toyonaka, Japan

[73] Assignee: Sumitomo Chemical Company, Limited, Osaka, Japan

[21] Appl. No.: 09/027,250

[22] Filed: Feb. 20, 1998

[30] Foreign Application Priority Data

Feb. 25, 1997 [JP] Japan ................................. 9-040593

[51] Int. Cl.[7] ............................ A01N 25/34; A01N 53/00
[52] U.S. Cl. ...................... 424/416; 106/15.05; 424/403; 424/405; 424/411; 424/412; 424/413; 428/219; 428/220; 428/532; 428/537.5; 428/907; 514/531; 560/124
[58] Field of Search ...................... 106/15.05; 424/403, 424/416, 411, 412, 413, 405; 514/531; 560/124; 428/219, 220, 532, 537.5, 907

[56] References Cited

U.S. PATENT DOCUMENTS

| | | | |
|---|---|---|---|
| 4,889,872 | 12/1989 | Naumann et al. | 514/531 |
| 5,002,183 | 3/1991 | Okano | 206/287 |
| 5,595,747 | 1/1997 | Kuroda et al. | 424/405 |
| 5,653,990 | 8/1997 | Iwasaki et al. | 424/405 |
| 5,756,522 | 5/1998 | Tomioka et al. | 514/340 |

FOREIGN PATENT DOCUMENTS

| | | |
|---|---|---|
| 0210416 | 2/1987 | European Pat. Off. . |
| 0576270 A1 | 12/1993 | European Pat. Off. . |
| 0775441 A1 | 5/1997 | European Pat. Off. . |
| 0792581 A1 | 9/1997 | European Pat. Off. . |
| 203271 | 2/1988 | Hungary . |
| 9700390 | 8/1998 | Hungary . |
| 6-9318 | 1/1994 | Japan . |

OTHER PUBLICATIONS

Chemical Abstract No. 126:3097, abstract of WIPO patent specification No. 96/32843, Oct. 1996.
Chemical Abstract No. 128:267237, abstract of Japanese Patent Specification No. 10–095701, Apr. 1998.
JAPIO Patent Abstract No. JP409308421A, abstract of Japanese Patent Specification No. 09–08421, Dec. 1997.
WPIDS Abstracts No. 93–365096, abstract of Japanese Patent Specification No. 05–271017, Oct. 1993.
WPIDS Abstract No. 94–012160, abstract of Japanese Patent Specification No. 05–320013, Dec. 1993.
Patent Abstract of Japan, vol. 96, No. 006, Jun. 28, 1996, (JP 08 039511).
WPI/Derwent Publication, AN–95–228575, May 1995 (Abstract of JP 7/138101).

*Primary Examiner*—Anthony Green
*Attorney, Agent, or Firm*—Sughrue, Mion, Zinn, Macpeak & Seas, PLLC

[57] ABSTRACT

The present invention provides a fabric protectant having an excellent effect in preventing the hatching of eggs of fabric pest insects. The fabric protectant comprises a paper or paper-like sheet carrying 2, 3, 5, 6-tetrafluorobenzyl 1R-trans-2,2-dimethyl-3-(2,2-dichlorovinyl) cyclopropanecarboxylate (Transfluthrin) and 1-ethynyl-2-methyl-2-pentenyl 1R-cis, trans-chrysanthemate (Empenthrin).

17 Claims, No Drawings

FABRIC PROTECTANT

The present invention relates to a fabric protectant.

Usefulness of 2,3,5,6-tetrafluorobenzyl 1R-trans-2,2-dimethyl-3-(2,2-dichlorovinyl)cyclopropane-carboxylate (Transfluthrin) as an active ingredient for a fabric protectant is known from JP-A-6-9318. Also, a fabric protectant containing 1-ethynyl-2-methyl-2-pentenyl 1R-cis,trans-chrysanthemate (Empenthrin) is currently commercially available.

For controlling a fabric pest insects, however, it is important to give consideration not only to the insecticidal effect, repellent action and clothes-eating protection against fabric pest insects (such as the larvae of casemaking clothes moth and webbing clothes moth), which have conventionally been studied, but also to the efficacy of preventing hatch of eggs of the fabric pest insect. The object of the present invention is to provide an excellent fabric pest insects controlling composition having also an effect of preventing hatch of the eggs.

The present invention provides fabric protectant comprising a sheet carrying Transfluthrin and Empenthrin. This invention also provides a method for controlling fabric pest insects and for protecting fabric (ex. clothes) by using the fabric protectant. This fabric protectant of the invention not only has the insecticidal effect, repellent action and clothes-eating protection against fabric pest insects but also shows an excellent inhibitory effect against hatch of the eggs of the fabric pest insects.

In the present invention, the sheet carrying Transfluthrin and Empenthrin preferably has a thickness of 0.1 to 4 mm and a bulk density of 0.2 to 0.7 g/cm$^3$, and the mixing ratio by weight of Transfluthrin to Empenthrin in the sheet is preferably in the range from 5:95 to 95:5. The bulk density is an index relating to a strength and opacity, and refers to a weight per unit volume of paper, namely relative density in g/cm$^3$. The calculation is effected by the following formula:

$$\text{Bulk density (g/cm}^3\text{)} = [\text{basis weight (g/cm}^2\text{)/thickness (mm)}] \times 1000$$

As the sheet in the present invention, there may be used not only pulp paper such as card board and filter paper but also paper like material made of vegetable fiber materials other than pulp, such as cotton linters. The size of the sheet is preferably about 10 cm to about 1 m in each length and width, for example in the case of using in a dresser, which may be one suitable for a state to be used. The sheet of several centimeters by several meters can be used.

The fabric protectant of the present invention can be produced, for instance, by dissolving Transfluthrin and Empenthrin in a solvent, for example, a ketone such as acetone, an alcohol such as methanol and ethanol, a halogenated hydrocarbon such as dichloroethane, an ether such as tetrahydrofuran and dioxane, an ester such as ethyl acetate, or a hydrocarbon such as hexane, kerosine and petroleum benzine, and having this solution carried on or in a sheet by coating, impregnation or other means. The total amount of Transfluthrin and Empenthrin carried by the sheet is usually about 0.1 to 100 mg/cm$^3$. When these compounds are dissolved in a solvent to prepare a solution to be carried on or in a sheet, there may be added an emulsifier, dispersant, spreading agent, stabilizer and other adjuvants. It is also possible to add other insecticide, synergist, anti-mold agent and the like.

The fabric protectant according to the present invention is effective for controlling the fabric pest insects such as those belonging to the genus Tineola such as a webbing clothes moth, the genus Tinea such as casemaking clothes moth, the genus Trichophaga such as tapestry clothes moth, the genus Attagenus such as black carpet beetle, and the genus Anthrenus such as varied carpet beetle. The fabric protectant of the present invention may be used in various ways; usually, it is placed in the vicinity of fabric at ordinary temperature and for instance, it may be directly placed in a cabinet drawer, or may be packed in an appropriate container and slung up in a wardrobe. The effective amount of the fabric protectant of the present invention used is usually about 1 to 10 g (in total amount of Transfluthrin and Empenthrin) per 1 m$^3$ of space.

The mixed insecticidal composition comprising Transfluthrin and Empenthrin can be used in various forms of preparation such as mosquito coil, electric mosquito-repellent mat, aerosol, oil solution and emulsifiable concentration, with their additive insecticidal effect but in the form of use as a fabric protectant according to the present invention, the insecticidal effect is exhibited synergistically in inhibiting hatch of the eggs of the fabric pest insects.

EXAMPLES

Preparation examples of the fabric protectant of the present invention and a test example thereof are shown below.

Example 1

An acetone solution of 50 mg each of Transfluthrin and Empenthrin was dropped onto and impregnated in a 34 cm×58 cm sheet of paper (filter paper) having a thickness of 0.2 mm and a bulk density of 0.5 g/cm$^3$, and the sheet was air dried to obtain a fabric protectant of the present invention.

Example 2

An acetone solution of 50 mg each of Transfluthrin and Empenthrin was dropped onto and impregnated in a 2.2 cm×3.5 cm sheet of paper (made of cotton linters) having a thickness of 2.5 mm and a bulk density of 0.4 g/cm$^3$, and the sheet was air dried to obtain a fabric protectant of the present invention.

The preparation of the fabric protectant used for comparison in Example 3 (test example) described below is shown as Referential Examples 1 and 2.

Referential Example 1

In the process of Example 1, 100 mg of Transfluthrin alone was used instead of using 50 mg of Transfluthrin and 50 mg of Empenthrin to obtain a fabric protectant for comparison.

Referential Example 2

100 mg of Empenthrin alone was used instead of using 50 mg of Transfluthrin and 50 mg of Empenthrin in the process of Example 1, to obtain a fabric protectant for comparison.

Example 3

Eight of working clothes (made of 65% polyester and 35% cotton) were interposingly contained in two piles (4 clothes in each pile) in a 43 cm×73 cm×16 cm clothing box, and the fabric protectant obtained in Example 1, Referential Example 1 or Referential Example 2 was placed between the second and third clothes from the bottom in each pile.

After the lapse of the predetermined periods of time (4 weeks, 20 weeks and 40 weeks), several Petri dishes of 3.5 cm in diameter containing 10 eggs of webbing clothes moth (about one day after oviposition) with a 2 cm×2 cm wool muslin cloth were prepared and they were placed between the fabric protectant and the third cloth from the bottom of each pile, between the third and fourth clothes from the bottom each pile and on top of each pile of clothes in the said clothing box.

Then the clothing box was covered, and after leaving it in a room of 25° C. for one week, the state of hatching of the moth eggs was observed. The results are shown in Table 1 as the average of observations of the eggs at six locations.

The respective marks in the table have the following significances.

X: 50% or more of the eggs hatched.

Δ: 30 to not more than 50% of the eggs hatched.

○: 10 to not more than 30% of the eggs hatched.

◉: Less than 10% of the eggs hatched.

TABLE 1

|  | Hatch inhibiting effect | | |
| --- | --- | --- | --- |
|  | 4 weeks | 20 weeks | 40 weeks |
| Example 1 | ○ | ◉ | ◉ |
| Referential Example 1 | X | Δ | ◉ |
| Referential Example 2 | Δ | ◉ | X |
| No treatment | X | X | X |

Example 4

Eight of working clothes (made of 65% polyester and 35% of cotton) are interposingly contained in two piles (4 clothes in each pile) in a 43 cm×73 cm×16 cm clothing box, and the fabric protectant obtained in Example 2 is placed between the second and third clothes from the bottom in each pile. Then, two Petri dishes of 3.5 cm in diameter containing 10 eggs of webbing clothes moth (about one day after oviposition) with a 2 cm×2 cm wool muslin cloth are prepared and they are placed similarly to said fabric protectants mentioned above.

After the clothing box is covered and is stored in a room of 25° C. for one week, the inhibiting effect of the eggs can be obtained sufficiently.

The fabric protectant of the present invention exhibits an excellent synergistic effect in inhibiting hatch of the eggs of fabric pest insects and is very useful for repelling and preventing breeding of fabric pest insects.

What is claimed is:

1. A fabric protectant comprising a sheet comprising Transfluthrin and Empenthrin in the ratio of 5:95–95:5.

2. A fabric protectant according to claim 1, wherein the sheet has a thickness of 0.1 to 4 mm and a bulk density of 0.2 to 0.7 g/cm$^3$.

3. A fabric protectant according to claim 1 or 2, wherein the total amount of Transfluthrin and Empenthrin carried by the sheet is 0.1 to 100 mg/cm$^3$.

4. A method for controlling fabric pest insects comprising utilizing the fabric protectant set forth in claim 1 or 2.

5. A method for preventing the hatching of eggs of a fabric pest insect comprising utilizing the fabric protectant set forth in claim 1 or 2.

6. A method for protecting a fabric comprising utilizing the fabric protectant set forth in claim 1 or 2.

7. A method for controlling fabric pest insects comprising utilizing the fabric protectant set forth in claim 3.

8. A method for preventing the hatching of eggs of a fabric pest insect comprising utilizing the fabric protectant set forth in claim 3.

9. A method for protecting a fabric comprising utilizing the fabric protectant set forth in claim 3.

10. A method set forth in claim 6, comprising placing the fabric protectant in the vicinity of fabric.

11. A method set forth in claim 6, comprising placing the fabric protectant in a cabinet drawer.

12. A method set forth in claim 6, comprising placing the fabric protectant in a wardrobe.

13. A method set forth in claim 6, comprising placing the fabric protectant in a container with fabric.

14. A method set forth in claim 9, comprising placing the fabric protectant in the vicinity of fabric.

15. A method set forth in claim 9, comprising placing the fabric protectant in a cabinet drawer.

16. A method set forth in claim 9, comprising placing the fabric protectant in a wardrobe.

17. A method set forth in claim 9, comprising placing the fabric protectant in a container with fabric.

* * * * *